(12) United States Patent
Matthison-Hansen et al.

(10) Patent No.: US 10,646,107 B2
(45) Date of Patent: May 12, 2020

(54) ENDOSCOPE WITH A TOOL

(71) Applicant: AMBU A/S, Ballerup (DK)

(72) Inventors: Kaspar Mat Matthison-Hansen, Helsingør (DK); Thomas Bachgaard Jensen, Copenhagen V (DK); Jakob Bønnelykke Kristensen, Ølstykke (DK); Lasse Kjeld Gjøske Petersen, Frederiksværk (DK)

(73) Assignee: AMBU A/S, Ballerup (DK)

( * ) Notice: Subject to any disclaimer, the term of this patent is extended or adjusted under 35 U.S.C. 154(b) by 288 days.

(21) Appl. No.: 15/576,812

(22) PCT Filed: May 26, 2016

(86) PCT No.: PCT/DK2016/050154
§ 371 (c)(1),
(2) Date: Nov. 25, 2017

(87) PCT Pub. No.: WO2016/188543
PCT Pub. Date: Dec. 1, 2016

(65) Prior Publication Data
US 2018/0296068 A1    Oct. 18, 2018

(30) Foreign Application Priority Data

May 27, 2015   (DK) ................................ 2015 70322

(51) Int. Cl.
*A61B 1/00*   (2006.01)
*A61B 1/005*   (2006.01)
(Continued)

(52) U.S. Cl.
CPC ............ *A61B 1/0052* (2013.01); *A61B 1/008* (2013.01); *A61B 1/00045* (2013.01);
(Continued)

(58) Field of Classification Search
None
See application file for complete search history.

(56) References Cited

U.S. PATENT DOCUMENTS

| 609,570 A | 8/1898 | Bowden |
| 4,203,430 A | 5/1980 | Takahashi |

(Continued)

FOREIGN PATENT DOCUMENTS

| AU | 2008207558 A1 | 4/2009 |
| CN | 1125390 | 6/1996 |

(Continued)

OTHER PUBLICATIONS

Danish Patent and Trademark Office Search Report for Appl No. PA201570322 dated Aug. 25, 2015, 7 pages.

(Continued)

*Primary Examiner* — Timothy J Neal
(74) *Attorney, Agent, or Firm* — Faegre Drinker Biddle & Reath LLP

(57) ABSTRACT

An endoscope having a handle with a handle housing arranged at a proximal end of the endoscope and an insertion tube extending from said handle and terminating in a tip part of a bending section at the distal end of the endoscope, the bending section comprises a distal tubular end segment and a plurality of articulated bending segments, the bending section comprises an intermediate segment between the proximal distal end segment and the plurality of articulated bending segments, wherein the intermediate segment is longer than a bending segment and the distal end segment.

17 Claims, 13 Drawing Sheets

Figure 1:
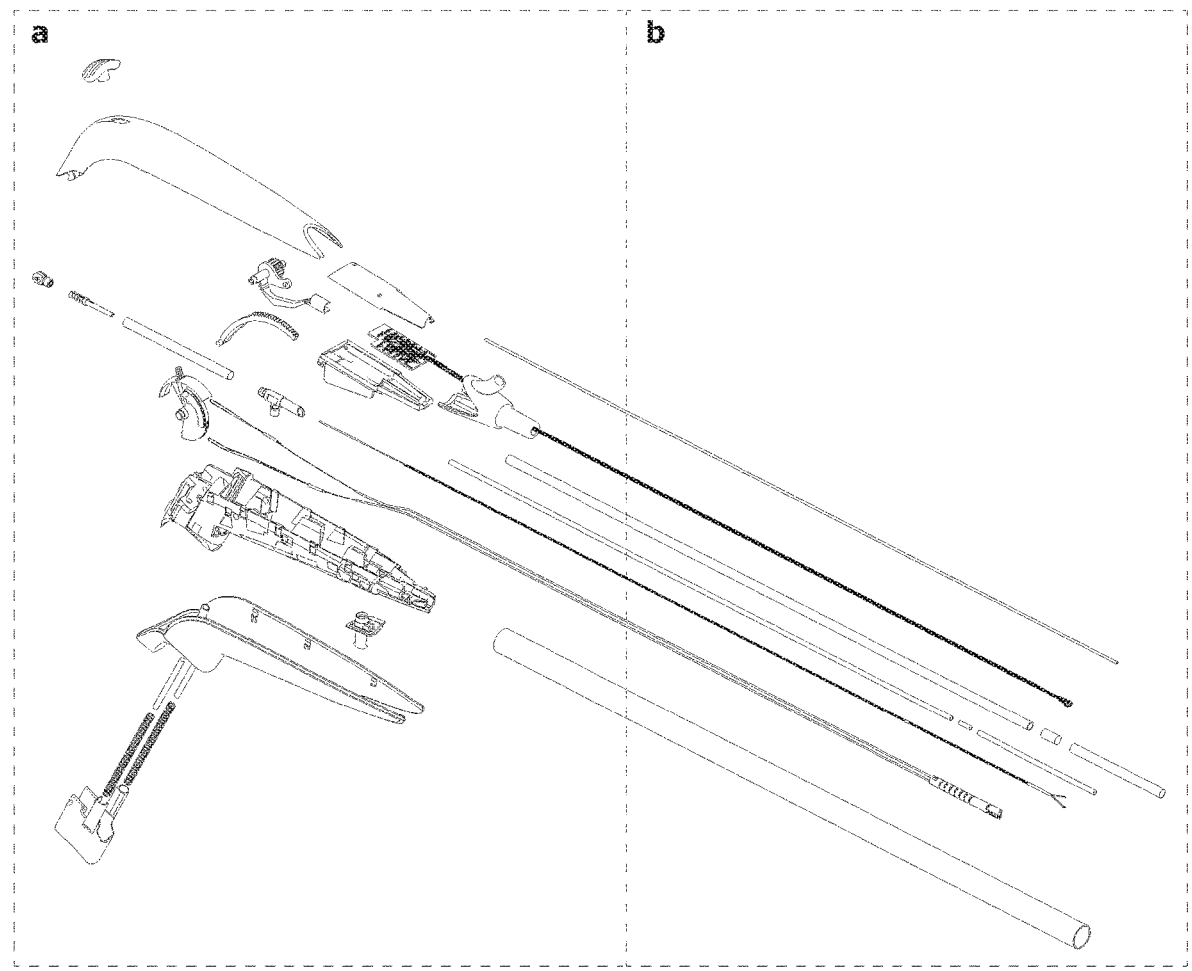

(51) Int. Cl.
  *A61B 1/008* (2006.01)
  *A61B 1/018* (2006.01)
  *A61B 1/06* (2006.01)
  *A61B 1/05* (2006.01)

(52) U.S. Cl.
  CPC ........ *A61B 1/00052* (2013.01); *A61B 1/0055* (2013.01); *A61B 1/0057* (2013.01); *A61B 1/00066* (2013.01); *A61B 1/00087* (2013.01); *A61B 1/00103* (2013.01); *A61B 1/018* (2013.01); *A61B 1/05* (2013.01); *A61B 1/051* (2013.01); *A61B 1/0676* (2013.01); *A61B 1/0684* (2013.01)

(56) References Cited

U.S. PATENT DOCUMENTS

| | | |
|---|---|---|
| 4,750,475 A | 6/1988 | Yoshihashi |
| 4,757,827 A | 7/1988 | Buchbinder et al. |
| 4,805,596 A | 2/1989 | Hatori |
| 5,167,221 A | 1/1992 | Chikama |
| 5,275,151 A | 1/1994 | Shockey et al. |
| 5,299,562 A | 4/1994 | Heckele et al. |
| 5,373,317 A | 12/1994 | Salvati et al. |
| 5,435,805 A | 7/1995 | Edwards et al. |
| 5,450,851 A | 9/1995 | Hancock |
| 5,462,527 A | 10/1995 | Stevens-Wright et al. |
| 5,810,876 A | 9/1998 | Kelleher |
| 5,879,289 A | 3/1999 | Yarush et al. |
| 5,938,588 A | 8/1999 | Grabover et al. |
| 6,007,531 A | 12/1999 | Snoke et al. |
| 6,077,277 A | 6/2000 | Mollenauer et al. |
| 6,258,101 B1 | 7/2001 | Blake et al. |
| 6,270,508 B1 | 8/2001 | Klieman et al. |
| 6,390,972 B1 | 5/2002 | Speier et al. |
| 8,790,250 B2 | 7/2014 | Petersen |
| 2002/0099266 A1 | 7/2002 | Ogura et al. |
| 2003/0009176 A1 | 1/2003 | Bilitz |
| 2005/0070764 A1 | 3/2005 | Nobis et al. |
| 2005/0075539 A1 | 4/2005 | Schulz et al. |
| 2005/0273085 A1 | 12/2005 | Hinmani et al. |
| 2006/0025651 A1 | 2/2006 | Adler et al. |
| 2006/0173243 A1* | 8/2006 | Watanabe ............ A61B 1/0055 600/141 |
| 2006/0258955 A1 | 11/2006 | Hoffman et al. |
| 2007/0219411 A1 | 9/2007 | Dejima et al. |
| 2007/0250038 A1 | 10/2007 | Boulais |
| 2007/0282167 A1 | 12/2007 | Barenboym et al. |
| 2008/0051631 A1 | 2/2008 | Dejima et al. |
| 2008/0188868 A1 | 8/2008 | Weitzner et al. |
| 2008/0195128 A1 | 8/2008 | Orbay et al. |
| 2008/0249483 A1 | 10/2008 | Slenker et al. |
| 2008/0287735 A1 | 11/2008 | Takemoto et al. |
| 2009/0054733 A1 | 2/2009 | Marescaux |
| 2009/0076328 A1 | 3/2009 | Root et al. |
| 2009/0209945 A1 | 8/2009 | Lobl et al. |
| 2009/0247994 A1 | 10/2009 | Bacher et al. |
| 2010/0022837 A1 | 1/2010 | Ishiguro et al. |
| 2010/0030020 A1 | 2/2010 | Sanders et al. |
| 2010/0249497 A1 | 9/2010 | Peine et al. |
| 2010/0268268 A1 | 10/2010 | Bacher et al. |
| 2010/0298642 A1 | 11/2010 | Trusty et al. |
| 2011/0009694 A1 | 1/2011 | Schultz et al. |
| 2011/0112517 A1 | 5/2011 | Peine et al. |
| 2011/0264129 A1 | 10/2011 | Holdgate et al. |
| 2011/0306831 A1 | 12/2011 | Kohnke et al. |
| 2012/0116362 A1* | 5/2012 | Kieturakis ............ A61B 17/29 606/1 |
| 2014/0073855 A1 | 3/2014 | Kindler |
| 2014/0142377 A1 | 5/2014 | Yang et al. |
| 2014/0148759 A1 | 5/2014 | MacNamara et al. |
| 2014/0206936 A1 | 7/2014 | Cooper et al. |
| 2014/0221749 A1 | 8/2014 | Grant et al. |
| 2014/0243615 A1 | 8/2014 | Schaeffer et al. |
| 2014/0275763 A1 | 9/2014 | King et al. |
| 2014/0316203 A1* | 10/2014 | Carroux ............ A61B 17/221 600/146 |
| 2014/0336532 A1 | 11/2014 | Seguy |
| 2015/0282701 A1 | 10/2015 | Oskin et al. |
| 2015/0366436 A1 | 12/2015 | Henrick |
| 2016/0095585 A1 | 4/2016 | Zergiebel et al. |
| 2016/0150946 A1 | 6/2016 | Tsumaru et al. |
| 2016/0348769 A1* | 12/2016 | Siegal .................. A61B 1/008 |
| 2018/0296069 A1 | 10/2018 | Matthison-Hansen |
| 2018/0303315 A1 | 10/2018 | Matthison-Hansen |
| 2018/0303316 A1 | 10/2018 | Matthison-Hansen |
| 2018/0303317 A1 | 10/2018 | Matthison-Hansen |
| 2018/0303472 A1 | 10/2018 | Matthison-Hansen et al. |
| 2018/0309908 A1 | 10/2018 | Matthison-Hansen et al. |

FOREIGN PATENT DOCUMENTS

| | | |
|---|---|---|
| CN | 1956684 A | 5/2007 |
| CN | 101513338 A | 8/2009 |
| CN | 102871636 | 1/2013 |
| CN | 103505176 | 1/2014 |
| CN | 203506676 U | 4/2014 |
| CN | 203885470 | 10/2014 |
| CN | 204120980 U | 1/2015 |
| EP | 0567146 A2 | 10/1993 |
| EP | 1484003 A1 | 12/2004 |
| EP | 1561413 A1 | 8/2005 |
| JP | H0910166 A | 1/2014 |
| WO | WO2005112806 A2 | 12/2005 |
| WO | WO2008033356 A2 | 3/2008 |
| WO | WO2008045374 A2 | 4/2008 |
| WO | WO2008061106 A1 | 5/2008 |
| WO | WO2010066789 A1 | 6/2010 |
| WO | WO2010066790 A1 | 6/2010 |
| WO | WO2013071938 A1 | 5/2013 |
| WO | WO2013106444 A1 | 7/2013 |
| WO | WO2014127780 A1 | 8/2014 |

OTHER PUBLICATIONS

International Search Report issued in PCT/DK2016050154, dated Aug. 8, 2016, 7 pages.

Written Opinion of the International Searching Authority for PCT/DK2016/050154 dated Aug. 4, 2016 in European Register, 6 pages.

Examination report in related Chinese application No. 2016800388599 dated Dec. 28, 2018, 9 pgs.

Examination report in related Chinese application No. 201680038859.9 dated Aug. 2, 2019, 9 pgs.

Search Report issued by the Chinese Patent Office, dated Mar. 3, 2020, for related Chinese Patent Application No. 201680038859.9; 9 pages.

* cited by examiner

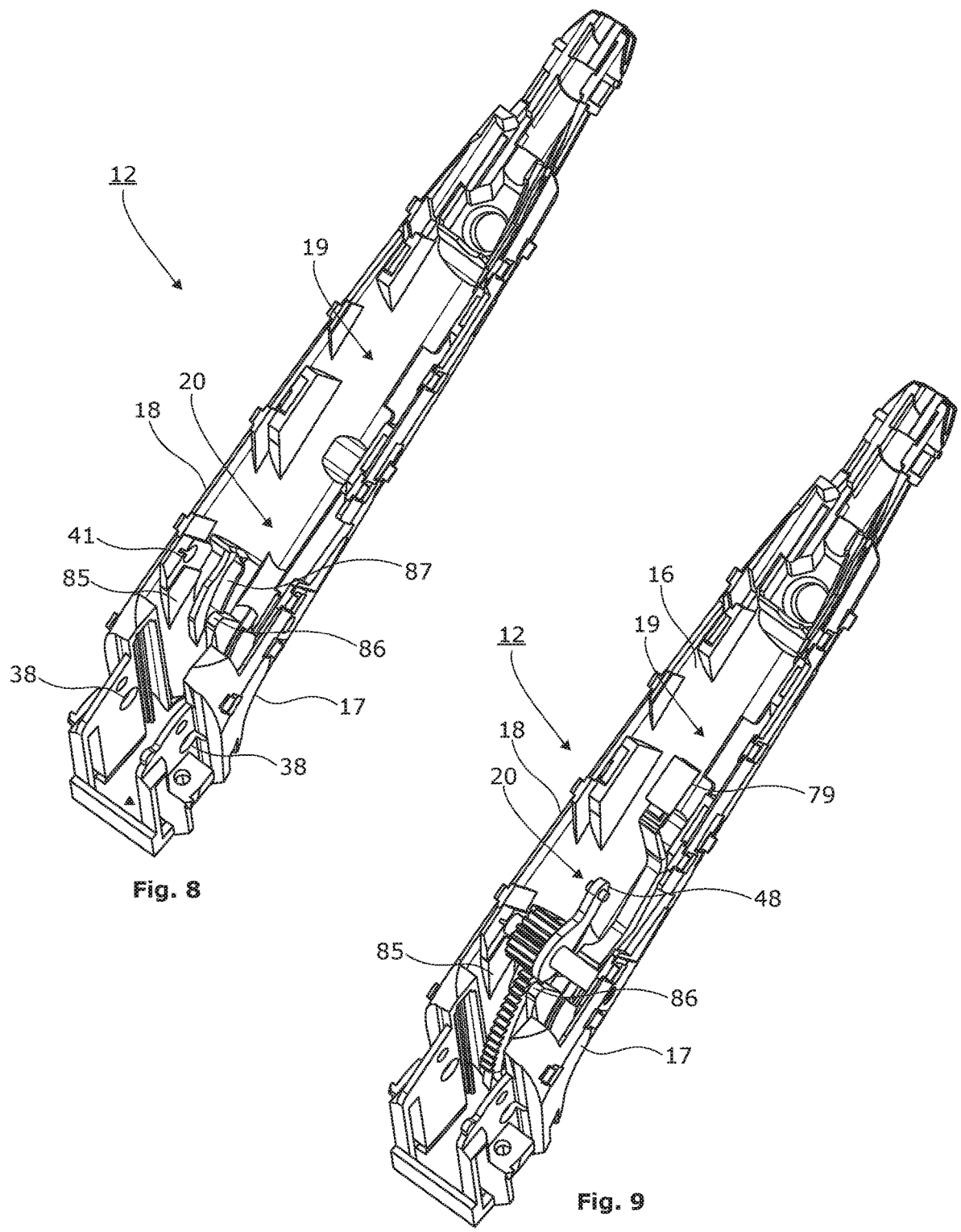

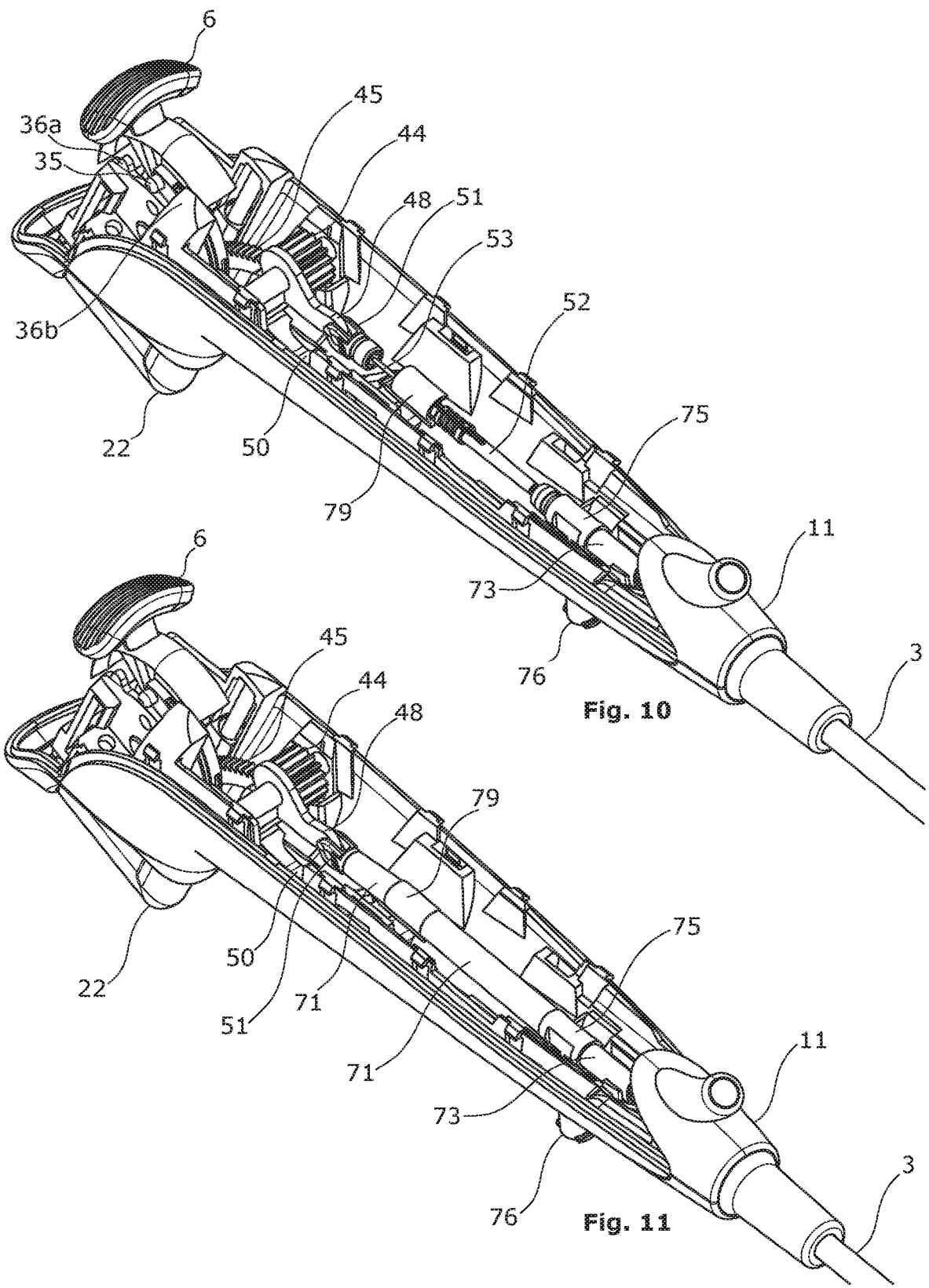

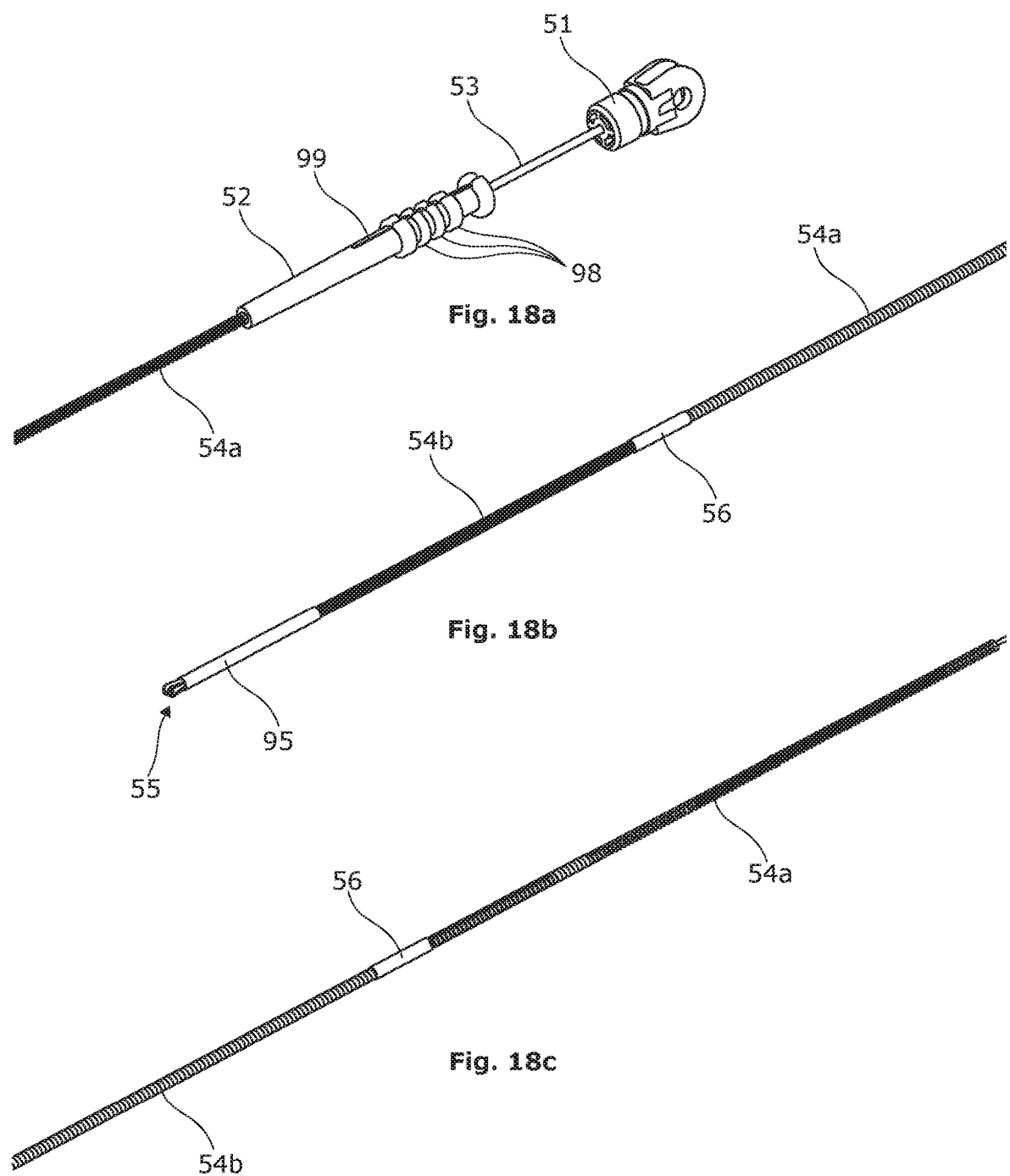

ENDOSCOPE WITH A TOOL

CROSS-REFERENCE TO RELATED APPLICATIONS

This is a § 371 application of International Application Number PCT/DK2016/050154, filed May 26, 2016, which claims priority from Denmark Patent Application Number PA 2015 70322, filed May 27, 2015, both applications incorporated herein by reference in their entirety.

The following applications disclose related subject matter: U.S. patent application Ser. No. 15/576,813, filed Nov. 25, 2017; U.S. patent application Ser. No. 15/576,814, filed Nov. 25, 2017; U.S. patent application Ser. No. 15/576,815, filed Nov. 25, 2017; U.S. patent application Ser. No. 15/576,816, filed Nov. 25, 2017; U.S. patent application Ser. No. 15/576,817, filed Nov. 25, 2017; and U.S. patent application Ser. No. 15/576,818, filed Nov. 25, 2017.

The present invention relates to an endoscope, in particular but not exclusively a disposable camera endoscope, having an operating handle arranged at a proximal end thereof and an insertion tube extending from said handle towards a distal end of the endoscope.

In general an endoscope comprises an operating handle at the proximal end and an insertion tube extending from the handle towards the distal end. The handle is adapted to be held by an operator and inter alia comprises externally protruding operating members connected to internal control means allowing the operator to control the movement of a bending section at the distal end of the insertion tube, while advancing the distal end of the insertion tube to a desired location e.g. within a body cavity of a person. By means of an attached monitoring device, such as a monitor with a display screen, the location to which the distal end has been advanced may be inspected using the endoscope. Often, however, inspection is not all that is desired, e.g. where the inspection is to locate the site for further actions. One such action could be the removal of an implanted stent, which necessitates the use of a tool.

In this respect WO2013/071938A1 discloses an endoscope with a built in tool in the form of a hook adapted to grip e.g. an urological stent, which can then be removed by retracting the endoscope. The endoscope is adapted for single handed use by an operator using the thumb to control the movement of the distal tip of the endoscope, and the index finger to control the reciprocating movement of the tool. The built in tool, however, does not allow other actions than gripping. The tool is controlled in a separate channel as compared to the working channel, through which fluid may be extracted or infused, or through which other tools may be inserted. Moreover, the full activation of the tool requires a reciprocating movement both out and in of the tip part of the bending section of the insertion tube of the endoscope. Given that stereoscopic vision is not available because only a single camera is used, it may be difficult for an operator to efficiently complete this reciprocating movement in a correct manner.

It is a further object of the present invention to provide an endoscope allowing the simultaneous control of the more complex actions of the integrated tool as well as the control of the bending section at the distal end of insertion tube of the endoscope using a single hand only.

It is a further object of the present invention to provide an endoscope allowing the simultaneous control of the more complex actions of the integrated tool during all operating conditions of the distal end of the insertion tube.

According to a first aspect of the invention this object is achieved by an endoscope having a handle with a handle housing arranged at a proximal end of the endoscope and an insertion tube extending from said handle and terminating in a tip part of a bending section at the distal end of the endoscope, the bending section comprises a distal end segment and a plurality of articulated bending segments, said endoscope further comprising a first operating member at the handle housing for controlling the bending section, a working channel extending within said insertion tube and having a distal end and a proximal end, a motion transfer member extending within said working channel and adapted to operate a retractable tool at an exit port of the distal end of the working channel at the tip part in response to the activation of a further operating member at the handle housing, the bending section comprises an intermediate segment between the distal end segment and the plurality of articulated bending segments, wherein the intermediate segment is longer than a bending segment.

The provision of an intermediate segment allows accommodation and protection of at least a part of the motion transfer member or the tool so that the tool may be released from the exit port and retracted properly under all operating conditions of both the tool and the distal top. Hence the endoscope may be operated without impairing operation of the tool or the bending radii. This is advantageous for all kinds of tools that may be envisaged to be used in combination with the invention, i.e. different tool types such as a pair grasping forceps, plyers, a needle, a stylet-cannula unit to carry out biopsies, brushes and scissors etc. Thereby the tool may be protected from being bend during operating of the bending section, i.e. during bending of the articulated bending segments in order to control the tip part, or to get stuck because it is protected in a part of the bending section where the working channel is not bended.

In a practically preferred embodiment the distal end segment is longer than a bending segment.

In a further practical embodiment which is especially advantageous for use in combination with a pair of grasping forceps, a distal end of said motion transfer member comprises a rigid tube section, which is more rigid than the rest of the motion transfer member. The intermediate segment ensure that the distal rigid tube section is not positioned in the articulated bending segments where it would be captured and difficult to release from the exit port at large bending radii.

In a practical embodiment that allows for improved bending properties of the articulated bending segments, the motion transfer member comprises a inner motion transfer member and an outer motion transfer member.

In a further practical embodiment that reduces friction between movable parts of the endoscope, the working channel is formed by a tube that comprises at least a first proximal section and a second distal section with a first connecting transition connecting the two sections, the second section has a higher degree of flexibility than the first section, and said outer motion transfer member comprises at least two sections differing from each other in rigidity and with a second connecting transition connecting the two sections, wherein the first connecting transition and the second connecting transition are staggered with respect to each other along the length of the insertion tube.

In yet another practical embodiment the movement of the first operating member is limited by the interior of the handle housing. This keep control of the bending radii and that bending radii are not determined by the cover of the operating handle, but by a predetermined configuration inside the operating handle.

In a further practical embodiment the handle housing comprises an interior chassis carrying the first operating member, and the chassis is provided with stop members limiting movement of the first operating member.

Figure 1A:
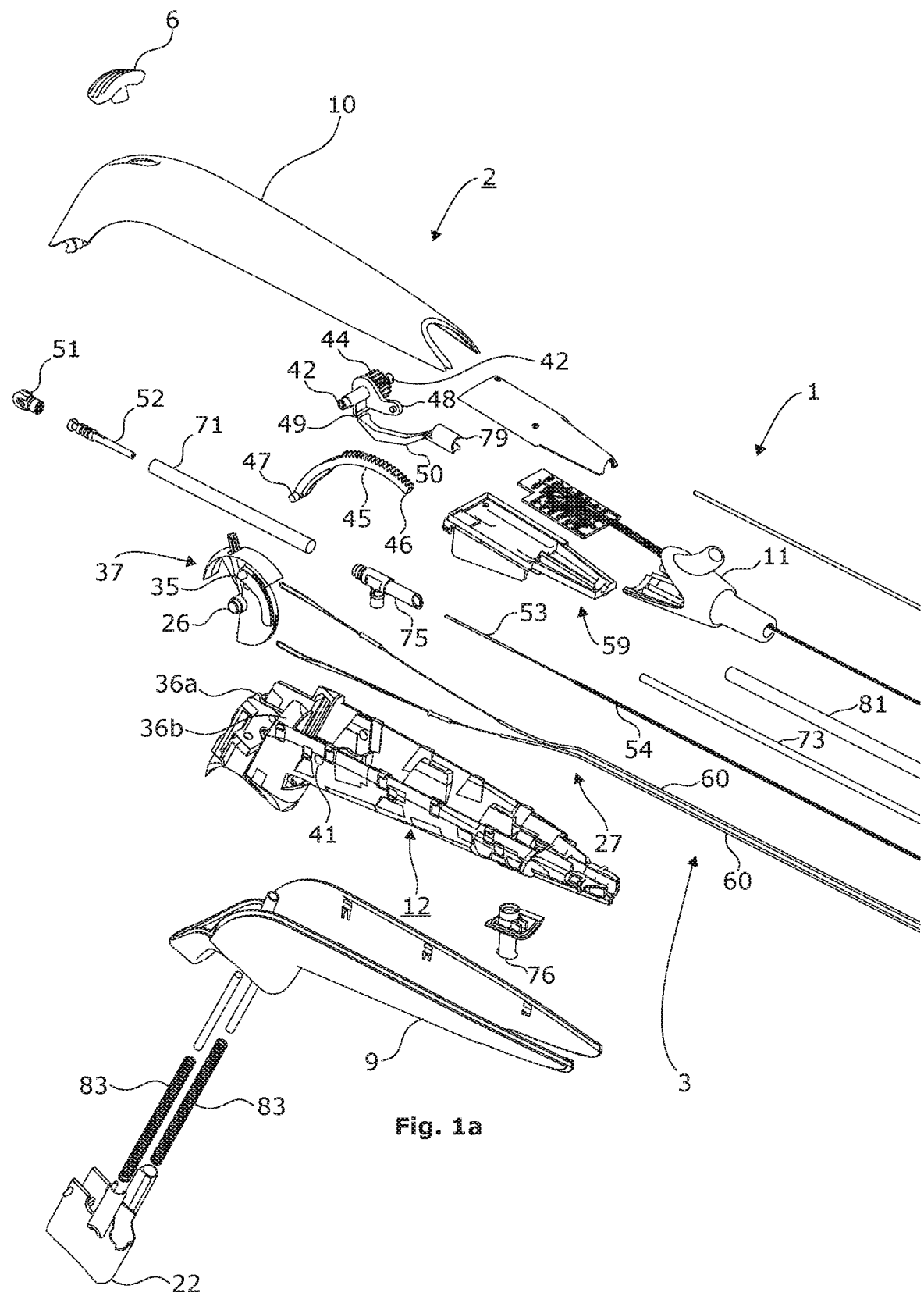
Figure 1B:
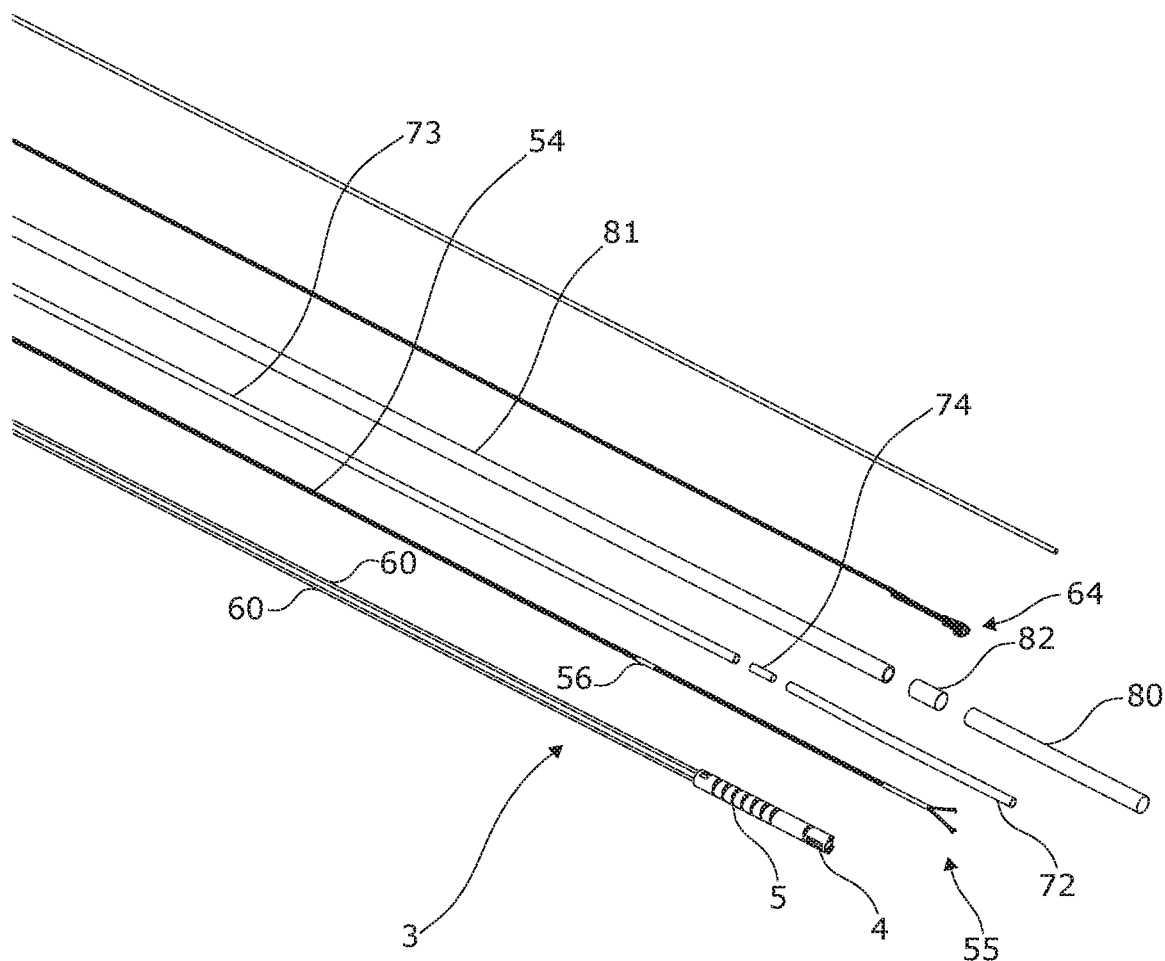
Figure 2:
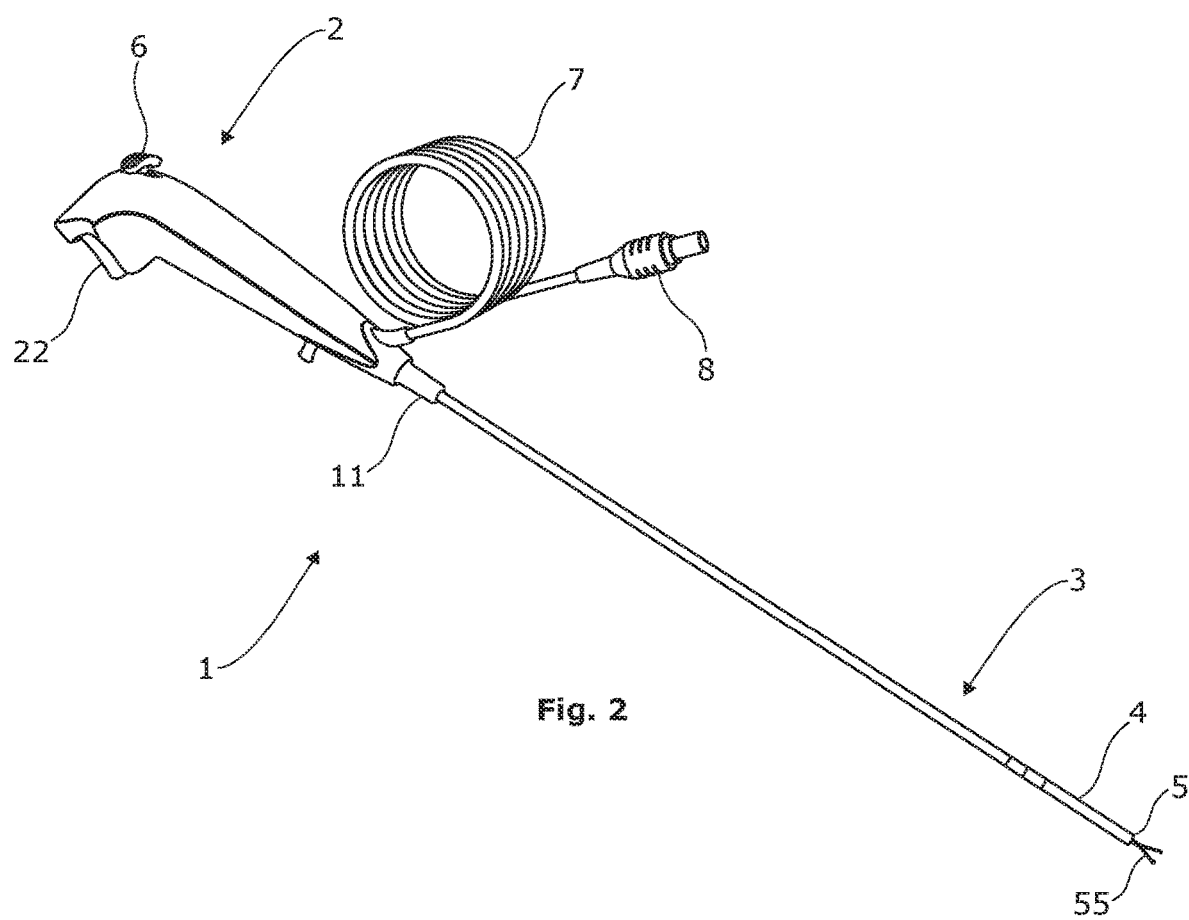
Figure 3:
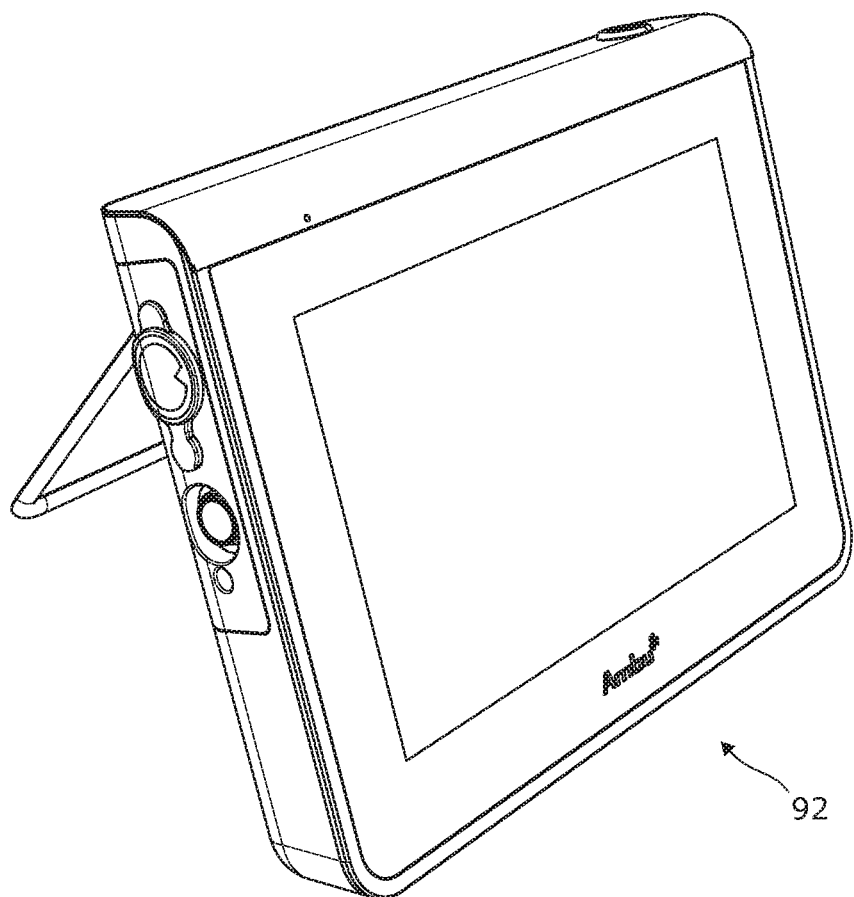
Figure 4A:
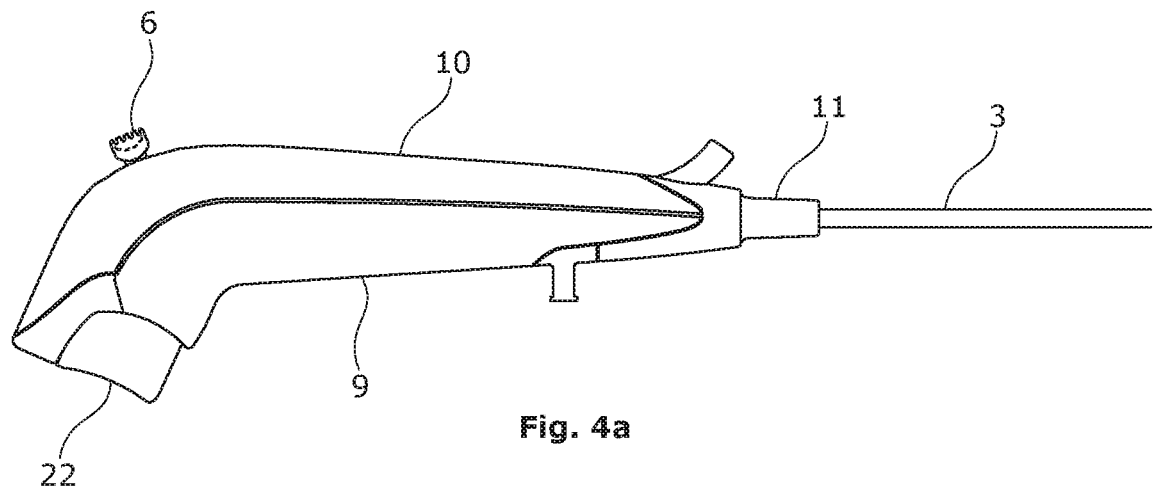
Figure 4B:
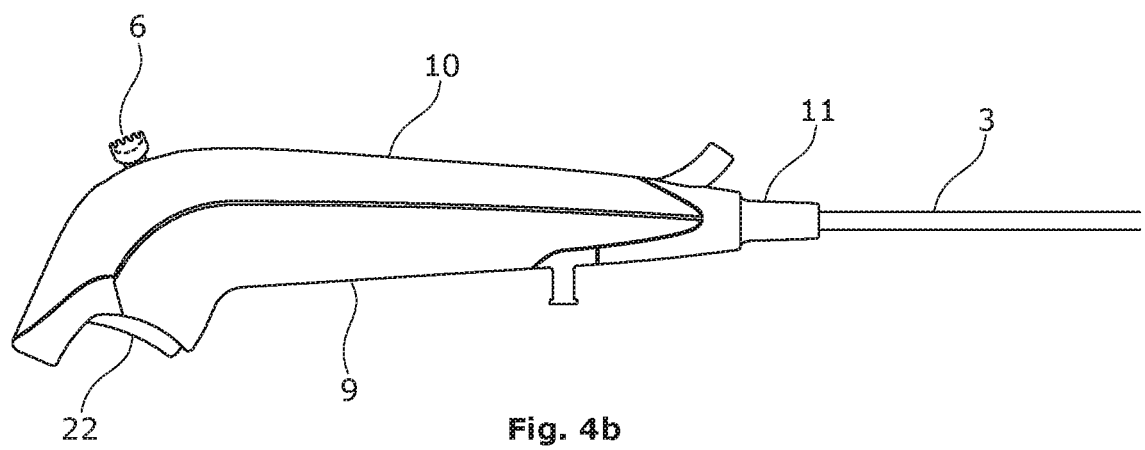
Figure 5:
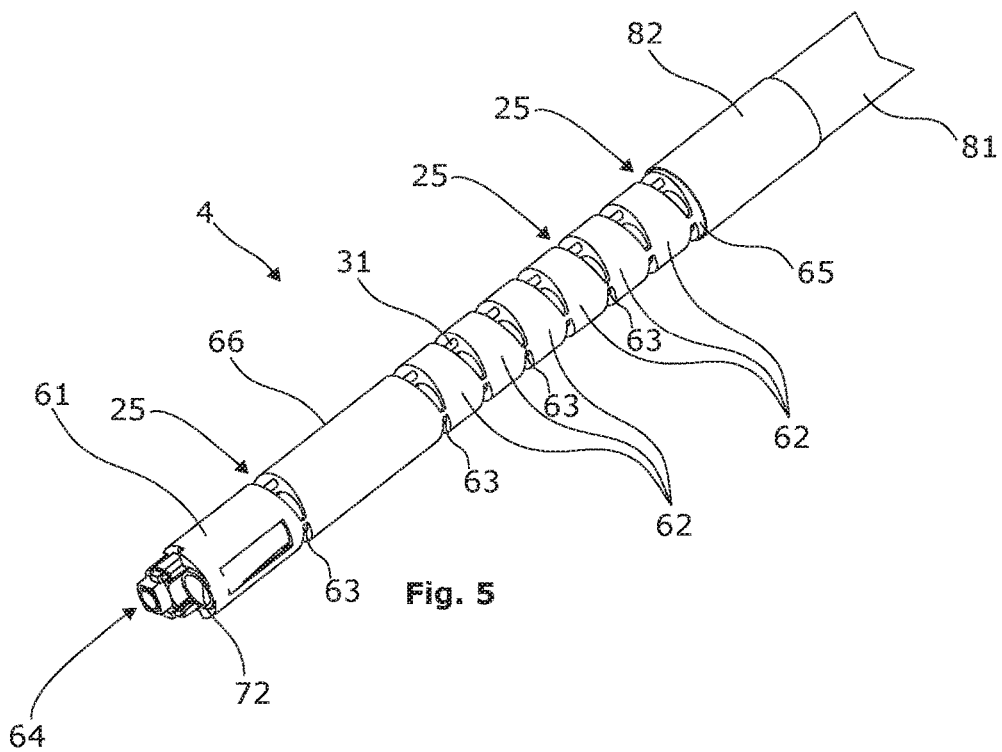
Figure 6:
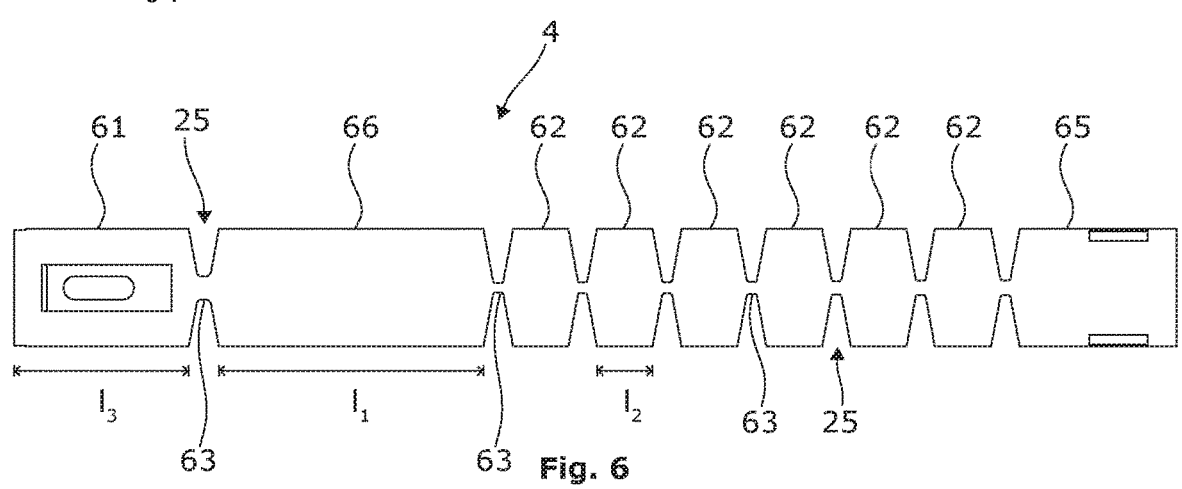
Figure 7:
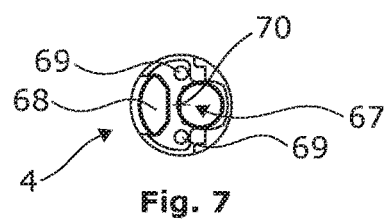
Figure 12:
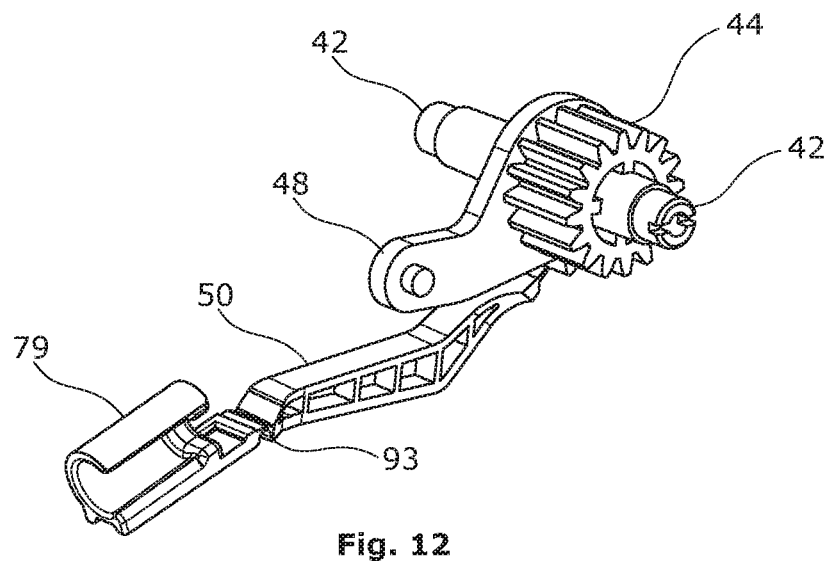
Figure 13:
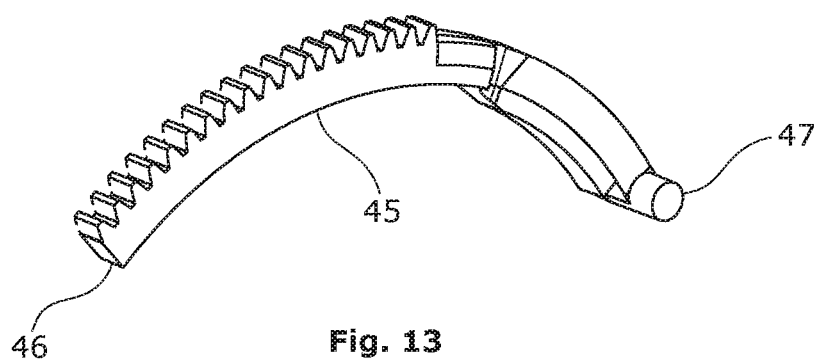
Figure 14:
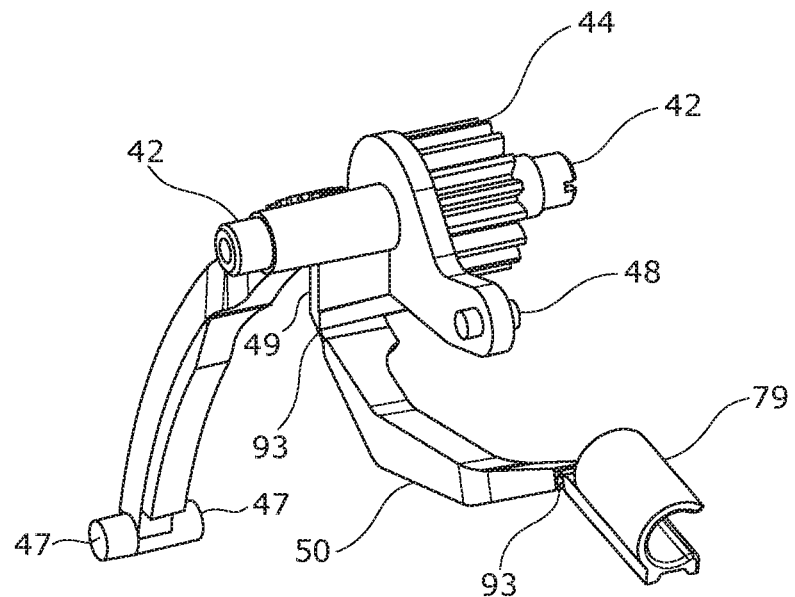
Figure 15:
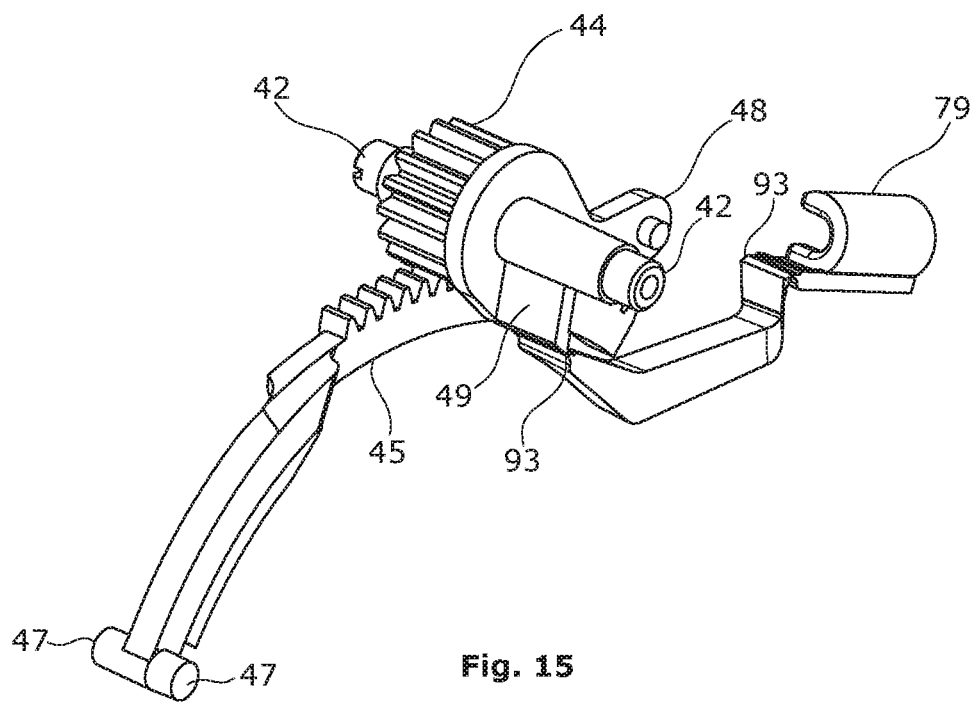
Figure 16:
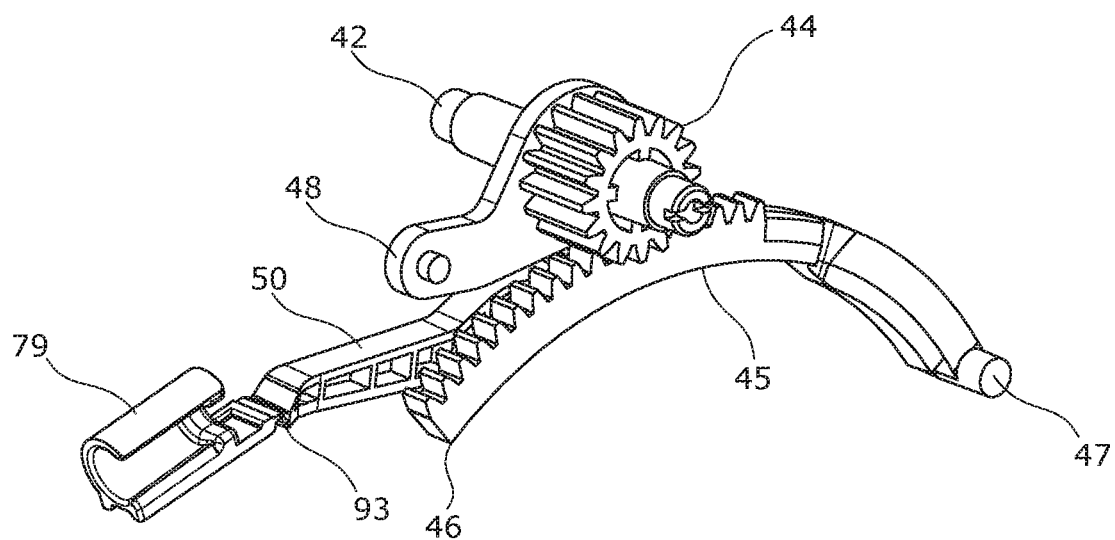
Figure 17:
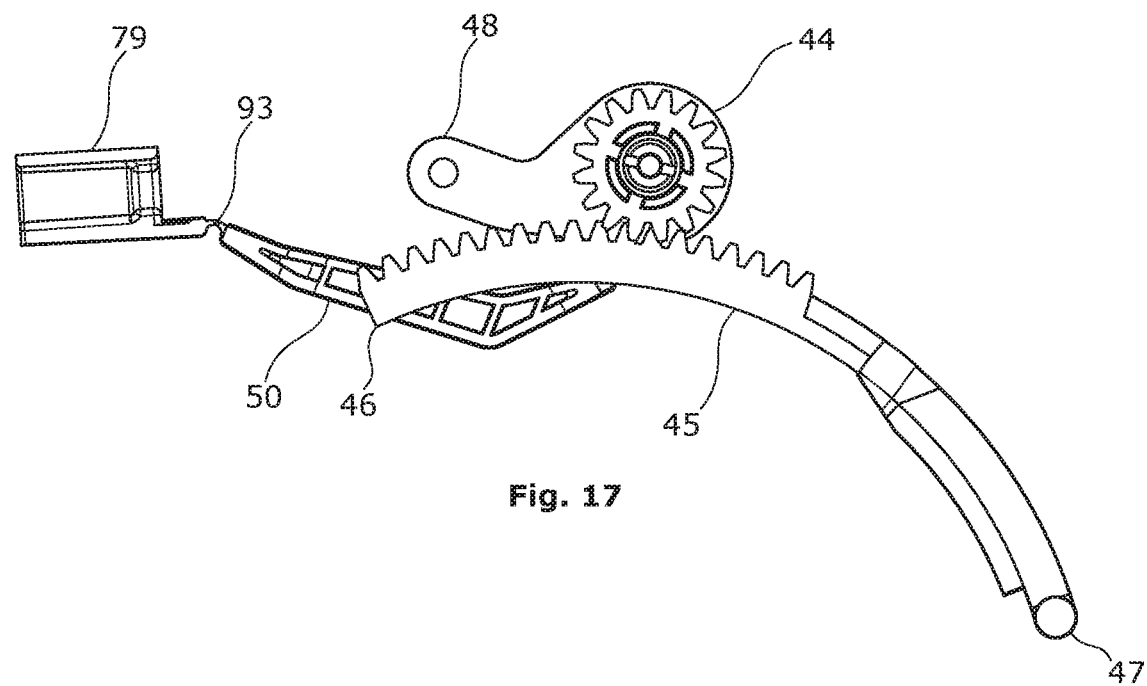

The invention will now be described in greater detail based on non-limiting exemplary embodiment and the drawing on which:

FIG. 1 shows an exploded overview of an endoscope according to the present invention and how this exploded view is split in a left-hand side part and a right-hand side part for better visibility in FIGS. 1a and 1b, FIG. 2 shows a perspective view of the fully assembled endoscope of FIG. 1, FIG. 3 shows a monitoring device for mutual connection with the endoscope of FIG. 1, FIG. 4a and FIG. 4b show partial views of the endoscope of FIG. 1 with the tool operating member in released and depressed state, respectively, FIG. 5 shows details of the insertion tube of the endoscope, FIG. 6 shows bending section of the endoscope, FIG. 7 shows a detail of the bending section, FIG. 8 shows show an internal chassis of the endoscope, FIG. 9 shows the chassis of FIG. 8 with a rack and pinion mounted, FIG. 10 shows the chassis of FIG. 9 partially mounted in the handle housing partially mounted in the handle housing and with rack and pinion of FIG. 9 attached to a motion transfer means, FIG. 11 corresponds to FIG. 10 but with the motion transfer means enclosed in a part of the working channel of the endoscope, FIG. 12 shows a first perspective view of the pinion of FIG. 9, FIG. 13 shows a perspective view of the rack of FIG. 12, FIG. 14 shows a second perspective view of the pinion of FIG. 9, FIG. 15 shows a first perspective view of the rack and pinion of FIG. 9 in mutual engagement, FIG. 16 shows a second perspective view of the rack and pinion of FIG. 9 in mutual engagement, FIG. 17 shows a plan view of the rack and pinion of FIG. 9 in mutual engagement, and FIGS. 18a-c show different sectors of motion transfer means comprising a first motion transfer member and a second motion transfer member.

Turning first to FIG. 2 an assembled endoscope 1 according to the present invention is shown. The endoscope 1 has a proximal end with an operating handle 2 to be held in one hand by an operator. Accordingly, the operating handle is shaped in a manner ergonomically suitable for operator, in particular but not exclusively for the hand of the operator, as arms and joints may also play a role in the ergonomics. From the handle 2 an insertion tube 3 extends towards the distal end of the endoscope. At the distal end of the endoscope 1 the insertion tube 3 ends in a bending section 4 and a tip part 5. The bending section 4 is in mechanical connection with a first operating member 6, digitally operable by the operator, e.g. by the thumb, thereby allowing the operator to bend the tip part 5 in a desired direction when advancing the insertion tube 3 towards a desired location, e.g. through a body cavity of a patient. In addition to the first operating member 6 the endoscope 1 comprises a tool operating member 22 adapted to operate a tool 55 at the tip part 5 of the endoscope 1. The tool operating member 22 is preferably in the form of a trigger or push-button so accommodated in the housing that it may be operated by the same hand as used for operating first operating member 6. In the configuration shown the first operating member 6 is adapted to be operated by the thumb of the operator whereas the push-button is adapted to be depressed independently thereof by the index finger of the very same hand of the operator. This allows singled handed use of the endoscope. As can be seen the push-button is has been partially depressed allowing the tool 55 to be advanced forwardly from the distal end of the tip 5 of the endoscope 1. This partially depressed position which will be described in greater detail later is an intermediate position between the fully released position shown in FIG. 4a, towards which the push-button is preferably spring biased, and the fully depressed position shown in FIG. 4b, which will also be described later.

As can also be seen in FIG. 2, the endoscope 1 comprises a flexible connection cable 7 with a connector 8 allowing the endoscope 1 to be connected to a monitoring device such as a monitor 92 shown in FIG. 3 forming part of an endoscope 1 and monitor 92 system.

Turning now to FIGS. 1, 1a and 1b an exploded view of the endoscope 1 is shown. As mentioned, the endoscope 1 has an operating handle 2 at the proximal end thereof i.e. at the left-hand side of FIG. 1a. The operating handle 2 is assembled from and comprises a number of handle parts to be described later. From the operating handle 1, the insertion tube 3 comprising a number of insertion tube parts to be described later extends towards the distal end of the endoscope, i.e. towards the right-hand side of FIG. 1b. The first operating member is is connected to a control lever 37 which is mounted in the handle 1 by means of trunnions 26 positioned in pivotal bearing 38 (cf. FIG. 8). The control lever 37 allows maneuvering of the bending section 4 via a Bowden cable arrangement 27 comprising pull-wires 31 and outer guide tubes 60. The control lever 37 is attached to the first operating member 6, and at least the first operating member 6 extends to the outside of the endoscope handle 2 through a slit in the shell part 10 to be accessible by a thumb of the an operator. As can be seen in FIG. 1a the control lever 37 may be provided with a protruding tap 35 for limiting movement of the control lever 37 and thereby the bending radius of the bending section 4. This is achieved by providing the interior of the operating handle 2 with one or more stop members 36a, 36b that limit movement of the control lever 37 by only allowing movement of the tap 35 between the two stop members.

The operating handle 2 comprises at least two shell parts 9, 10 forming the outer housing walls of the handle housing of the operating handle 2. The two shell parts 9, 10 form the outer housing walls and are shaped to provide an ergonomically suitable operating handle for an operator, gripping it with one hand. In addition to the two shell parts 9, 10 a transition part 11 forming the transition from the operating handle to the insertion tube 3, may be provided. This transition part may also form part of the handle housing. However, the two shell parts 9, 10 constitute the major part of the housing in the embodiment shown. The shell parts 9, 10 and almost all other parts are mounted on a chassis 12.

Turning now to FIG. 5 details of the distal end of the insertion tube 3 with the articulated bending section 4 is shown. Some parts, such as an external sheath 80 normally covering the bending section 4, have been removed for clarity. The bending section comprises a number of segments 61, 62, 65, 66. More specifically a distal end segment 61, a proximal end segment 65 (not fully visible in FIG. 5), a plurality of articulated bending segments 62 and an intermediate segment 66. In the illustrated embodiment, the number of bending segments 62 are is six, but the skilled person will understand that the precise number is less important. The distal end segment 61 is tubular shaped with an interior end wall towards the intermediate segment 66. The interior end wall is provided with through holes for fastening the pull wires 31. I.e. distal end segment 61 has a generally circular cross section with one passage from the end wall to the most distal part. The end wall is adapted with openings to allow passage of electrical supply wires and pull-wires. The tubular shape allows the distal end segment 61 to least partially accommodate a camera module 64 comprising a camera, light emitting diodes and electronic circuits as well as it accommodated a portion of a tube 72 forming a part of a working channel. The working channel extends inside the insertion tube 3 all the way from the distal tip part 5 to the operating handle 13 and is formed by tube 72 and tube 73, which are connected by a connecting tube member 74. The working channel may via a suction port 76 on the handle be connected to a standard external suction, e.g. wall suction present in hospital environment by means of an attached tube.

One embodiment of the bending section 4 is shown in FIG. 6 without any attached parts. It can be seen that there is one distal end segment 61, one proximal end segment 65, an intermediate segment 66 and six articulated bending segments 62. The bending segments 62 are interconnected by means of flexible hinge members 63 formed by cut-outs 25 between the hinge sections 62. As can be seen from FIGS. 5 and 6 the intermediate segment 66 is longer than the bending segments 62. Preferably, the intermediate segment 66 is also longer that the distal end segment 61. Hence in the embodiment of FIGS. 5 and 6 the intermediate segment 66 has a length $l_1$, which is longer than a length $l_3$ of the distal end segment 61 and a length $l_2$ of a bending segment 62, where the distal end segment 61 has a length $l_3$, which is longer that a length $l_2$ of a bending segment. In a preferred embodiment the length $l_1$ of the intermediate segment is about 1.5-3 times the length $l_3$ of the distal end segment and is 4-5 times the length $l_2$ of a bending segment.

The bending segments 62 generally have the same cross-section, which generally correspond to the end view of FIG. 7. That is to say a generally circular cross-section with four passages 67, 68, 69. The first passage 67 is circular and adapted to engage and support the outer wall of the tube 72 forming a portion of the working channel. This first passage is relatively large, and the centre 70 of the cross-section of the bending segments actually lies within the first passage 67. The second passage 68 is adapted to accommodate electrical supply wires for the camera module 64. The camera and the light emitting diodes are mounted on a small circuit board to which the supply and signal wires are connected. The last two passages are pull wire passages 69 for guiding pull wires 31 of a Bowden cable arrangement 27, where the pull wires are guided in outer guide tubes 60. The pull wire passages 69 are arranged symmetrically opposite each other on either side of the plane in which the hinge members 63 extend. Preferably, the intermediate segment 66 have the same cross-section as shown in FIG. 7, i.e. the same as the bending segments 62.

The ends of the pull-wires are secured in the distal end segment as well as connected to the control lever 6 in the operating handle 2. Thus by manipulating the control lever 6 the pull wire may be tensioned on one side of the plane of the hinge members 63 and slacked on the other, thus allowing the articulated bending section 4 to bend in a desired direction. The distal end segment preferably also has a number of cut-outs, preferably through holes. These help securing the camera module and the end of the tube 9 etc. when these are moulded-in by means of plastic material, e.g. in a process similar to the one described in WO-A-2010/066790 incorporated herein by reference. As seen in FIGS. 5 and 6 the bending section 4 is provided with a recess 25 between the distal end segment 61 and the intermediate segment 66. This most distal recess 25 is provided to facilitate assembly and fastening of the pull-wires to the distal end segment 61 in a preferred embodiment, wherein the tip part 5 is moulded as described above and where distal recess 25 is at least partly filled with moulding material for mounding the tip part 5 so that the distal end segment 61 and the intermediate segment 66 are fixed to each other in a non-articulated manner. Evidently, the pull-wires may be fastened to the proximal portion of the intermediate segment 66. Alternatively, the pull-wires may be affixed to via through holes at a proximal part of the intermediate segment where an outer surface of the intermediate segment is provided with apertures for allowing guidance of the pull-wires to and from the through holes during assembly of the pull-wires.

As best seen in FIG. 8, the chassis 12 preferably shell shaped, i.e. the chassis 12 comprises an essentially shell shaped structure with a shell wall having an inner surface 16 and an outer surface 17 linked by an edge 18, said essentially shell shaped structure defining an interior compartment 19 delimited by said inner surface 16 and the edge 18 of the shell wall, the edge thus defining main opening 20 of said interior compartment 19. It will be understood that the chassis 12 can be designed mainly based on technical requirements, in such as kinematic chains of movable parts to be described further below, and thus be optimized for those technical requirements without having to inherit constraints from the ergonomic requirements of the handle 2, i.e. the shape of the two shell parts 9, 10.

As mentioned above, the chassis 12 is adapted to for the mounting of almost all parts of the endoscope 1. In particular, the chassis 12 is adapted for holding movable parts forming of kinematic chain from the push-button forming the tool operating member to the motion transfer means transferring the movement of the tool operating member 22 to the tool 55.

One such adaptation is a pair apertures 41 in the form of essentially cylindrical through holes can be seen in FIG. 1a. The apertures 41 serve as bearings of trunnions 42 carrying rotary member such as a pinion 44, best visible in FIG. 12. As can be seen from FIGS. 15 to 17, the pinion 44 is adapted to be in engagement with a curved rack 45. The curved rack 45 is shown separately in FIG. 13. The curved rack 45 has a first free end 46 and a second end with trunnions 47 held loosely in suitable receptacles inside the push button forming the tool operating member 22. The rack 45 as such is loosely held in a guideway comprising a first side 85, a second side 86 and a curved bottom 87 adapted to keep the rack 45 in engagement with the pinion 44. The first side 85 and the second side 86 as well as the curved bottom 87 are preferably formed integrally with the remainder of the chassis 12, e.g. in an injection moulding process. The first side is preferably constituted by a plane surface of a thickened part of the wall, i.e. a raised part of the inner surface 16 of the chassis 12.

Rotation of the pinion 44 may be effected by an operator moving the push-button forming the tool operating member 22, e.g. depressing it using an index finger, upon which the push-button forming the tool operating member 22 transfer motion to the curved rack 45, in turn rotating the pinion 44.

On the pinion 44, two levers 48 and 49 are provided. These levers 48 and 49 are in rigid connection with the pinion 44. The levers 48 and 49 have different lengths so as to influence a first motion transfer member 53 and a second transfer member 54 of the motion transfer means in different ways in order to effect a compound movement of the tool 55. As will be described later this compound movement comprises both a linear movement of the tool 55 and a task movement of the tool 55.

As can best be seen in FIG. 1a, the first motion transfer member 53 is arranged co-axially within the second motion transfer member 54. The first motion transfer member 53 and the second motion transfer member 54, in turn, are arranged within in tubular members 71, 72, 73, 74, which form part of the working channel of the endoscope, together with an e.g. T- or Y-shaped bifurcated section 75 providing the entry port to the working channel.

As can best be seen from FIGS. 18a-18c the first and second motion transfer members 53, 54 each comprise different sectors with different rigidities or bending properties, matching the requirements of the insertion tube 3, and the working channel, which both also has different bending properties along the length thereof. The first motion transfer member 53 preferably comprises a rigid rod piece at the proximal end and a rod or tubular piece at the tool 55. Between the two, the first motion transfer means may comprise a flexible wire.

The first motion transfer member 53 is terminated in an end sealing means 51. Apart from sealing the proximal end of the working channel, the end sealing means also serves as part a first kinematic chain by being pivotally connected to the first lever 48.

The first kinematic chain is as follows: Depressing the tool operating member 22 will move the rack 45 in a curvilinear movement via the trunnions 47. The rack 45, which has teeth in permanent engagement with the pinion 44, will rotate the pinion 44 and the first lever 48 rigidly connected thereto. The rotating first lever will consequently push the proximal end of the first motion transfer member 53, causing the tool 55 arranged at distal end of the first motion transfer member 31 to be moved out of the working channel beyond the distal end of the insertion tube 3 of the endoscope 1. Being spring biased, by e.g. a pair coil springs 83 accommodated in the chassis 12, a release of the tool operating member 22 will automatically return the tool operating member 22 to the position of FIG. 4a.

The second motion transfer member 54 forms a sheath for the first motion transfer member and preferably comprises a coil spring part 54a wound from wire with a rectangular cross section towards the proximal end, and a coil spring part 54b wound from wire with a circular or round cross section towards the distal end. Preferably, the outer motion transfer member comprises at least two sections 54a, 54b differing from each other in rigidity and with a second connecting transition 56 connecting the two sections 54a, 54b. At the distal end, the secand motion transfer member is terminated in a rigid tubular member 95.

The second motion transfer member 54 is terminated in a first tubular end member 52. The rigid part of the first motion transfer member 53 passes coaxially trough the first tubular end member 52 and into the remainder of the second motion transfer member 54. The passage through the first tubular end member 52 as well as through the remainder of the second motion transfer member 54 is adapted to allow mutual lengthwise relative motion, i.e. mutually reciprocating movement.

Not unlike the sealing end member 51, the first tubular end member 52 serves as part of a second kinematic chain adapted to provide a different motion pattern of the second motion transfer member 54 as compared to the first motion transfer member 53 in response to the very same depression, i.e. one and the same as the one described above. This is achieved by the second lever 49 which is also rigidly attached to the pinion 44 but has a different length than the first lever 48. At the end of the second lever 49 a first arm 50 is provided in articulated connection with said second lever 49. The second end of the first arm 50 is in articulated connection with a clamping means 79 adapted to clamp the tubular end means 52 with a part 71 of the working channel wall interposed. The interposed part 71 is preferably a flexible hose part. Preferably, the flexible hose part is made from the very same tubular material as is used to form the outer sheath 80 of the insertion tube 3 at the distal end and around the bending portion 5. To ensure good grip between the interposed part of the working channel wall 71 and the first tubular end member 52 the first tubular end member may comprise concentric ribs 98 or corrugations, or similar means. The articulations of the first arm 50 are preferably provided as integrally moulded foil hinges 93, as best seen in FIG. 15.

Accordingly, the second kinematic chain is as follows: Depressing the tool operating member 22 will move the rack 45 in a curvilinear movement via the tool trunnions 47. The rack 45, which has teeth in permanent engagement with the pinion 44, will rotate the pinion 44 and the second lever 49 rigidly connected thereto, so as to change their relative position while remaining in the engagement. The rotating second lever 49 will consequently push the proximal end of the first arm 50, thereby moving clamping means 79 at distal end of the first arm 50, articulating the first arm 50 as necessary in the foil hinges 93. The clamping means 79 moves the clamped part of the working channel wall part 71. Being clamped, the clamped part of the working channel wall 71 moves the first tubular end member of the second motion transfer member 54 towards the distal end of the working channel, consequently causing the distal end of the second motion transfer member 54 to be moved out of the working channel beyond the distal end of the insertion tube 3 of the endoscope 1. The distal end of the second motion transfer member 54 is preferably terminated in a second tubular end member 95. Being spring biased, by e.g. a pair coil springs 83 accommodated in the chassis 12, a release of the tool operating member 22 will automatically return the tool operating member 22 to the position of FIG. 4a.

Providing these two different kinematic chains allows the tool 55 to perform a compound movement comprising both a linear movement and a task movement, during one continuous depression of the tool operating member 22. In the linear movement, the tool 55 is advanced to a position in front of the distal end of the insertion tube 3 of endoscope 1 where it is visible from the camera built into the tip part 4 of the endoscope 1, and hence visible by the operator on the monitor 92 attached to the endoscope via cable 7 and connector. This may be performed by only partially depressing the tool operating member 22, e.g. to the position shown in FIG. 2, where with a suitable layout of the first kinematic chain will not advance any further but remain stationary or at least almost stationary with respect to the distal end of the insertion tube 3 of the endoscope even if the tool operating member is depressed further. Having located the correct position for operating the tool 55, e.g. by laterally moving the tip 4 of the bending section 5 at the distal end of the insertion tube 3 of the endoscope 1 using the first operating member 6 simultaneously with the tool operating member, the task movement can be performed.

In the preferred embodiment the tool 55 at the distal end of the first motion transfer member 53 comprises a self expanding configuration, such as a pair of spring tweezers, forceps, a spring loop, or the like which as long as it is accommodated in the tubular member 95 is compressed, as shown in FIG. 18b. Accordingly, it will auto-expand if it is advanced out the second tubular member 95, to the configuration shown in FIG. 2. Now, due to the second kinematic chain operating independently of the first kinematic chain, the second motion transfer member is held stationary is in the working channel during the first part of the depression of the tool operating means 22 to the intermediate position. Then, still due to the independent operation of the first and second kinematic chains, continuing the continuous movement by further depressing of the tool operating member 22 will cause the second motion transfer member to also start moving thereby advancing the second tubular end member 95. Consequently, the second tubular end member 95 slides over the tool 55 again, because as mentioned above the first kinematic chain is laid out to keep the tool 55 stationary in the field of vision of the camera at a distance from the tip part 4 of the insertion tube 3 of the endoscope 1. This will the effect the task movement of closing the tool 55 because the configuration as show in FIG. 18b is now restored, but this time at the position at the location outside the working channel set at the intermediate depression of the tool operating member 22. Keeping this position is of outmost benefit for the operator, who having only one camera eye does not perspective vision and therefore as difficulties in judging distances. Thus, having found the position where a stent a other object is to be gripped, e.g. by touching them with the tool, the operator can do so without further advancing or retracting of the entire endoscope 1.

Having gripped object, such as a stent, with the tool 55 in this way the object may then be removed from the body by retracting the entire endoscope 1 from the cavity whilst holding the tool operating member 22 depressed.

For the sake of clarity it should be noted that the term continuous movement is merely to be understood as a movement of the tool operating member from released state to a depressed state. It does not imply that the movement cannot be paused by the operator during the continuous movement. It does also not imply that the movement cannot be partially reversed by the operator releasing the tool operating member 22, in the search for the gripping location. In fact a latch means may be included to partially intermit the procedure without the tool changing its position. This could be a simple click mechanism as is well known in the art, latching when the tool operating member 22 is depressed fully, and releasing upon repeated depression og the tool operating member 22. As mentioned above, and as can be seen from FIGS. 13 and 15-17 the rack 45 has a curvature. This curvature preferably matches the curvature of the curved bottom 87 of the guideway, so that the teeth of the rack 45 are kept in engagement with the matching teeth of the pinion 44. This curvature saves space helping to fit the rack 45 and pinion 44 mechanism within the chassis 12 and the handle housing 2. The skilled person will understand that the forces and torques of the kinematic chain may be also be influenced by suitable choice of curvature and length of the rack 45 and diameter of the pinion 44 provided it is generally circular. The pinion 44 with a generally oval shape or other curvature is also envisaged. The skilled person will also understand that the two kinematic chains, and in particular their mutual differences could be influenced by suitable choice of the length of the levers 48 and 49, their angular spacing on the pinion 44, and the length and articulations of the arm 50, as well as by the provision of further arms. This may allow specific adaptation of the kinematic chains to the specific requirements of different tools 55.

As will be understood from the above the first and second motion transfer members are located within the working channel of the endoscope 1, comprising tubular members 71, 72, 73, 74 forming a generally tubular working channel wall and an e.g. T- or Y-shaped bifurcated section 75 providing the entry port to the working channel.

Starting from the distal end of the endoscope 1, a first tubular member 72 adapted to comply with the bending requirements of the bending section 5 of the endoscope 1 is provided. The first tubular member 72 passes through the bending section and thus provides an exit port 96 of the working channel at the tip 4 thereof. Via a short joint tube 74, a second tubular member 73 is joined at one end with the first tubular member 72 and provides a longer intermediate section of the working channel. Hence the working channel is formed by a tube that comprises at least a first proximal section 73 and a second distal section 72 with a first connecting transition 74 connecting the two sections.

From the perspective view in FIG. 1b it is realized that it is preferred that the connecting transition member 74 of the working channel and the connecting transition member 56 of the second motion transfer member 54 are staggered with respect to each other along the length of the insertion tube 3. Hence when the second motion transfer member 54 is moved back and forth along the inside of the working channel the two transitions are staggered along the length of the insertion tube in all conditions of use.

The second tubular member 73 is generally more rigid than the first tubular member 72. The second tubular member 73 is however still quite flexible. More specifically, the second tubular member 73 and a second outer tube section 81 surrounding it are so flexible that they allow a loose knot to be tied on the insertion tube 3. The alternative is a rigid or semi-rigid endoscope where the insertion portion is rigid, only slightly bendable or hinged, and which does not allow a knot to be tied on the insertion tube. It is preferred to make the first tubular member 71 of a first polyurethane elastomer and to make the first tubular member 72 of another polyurethane elastomer. Both polyurethane elastomers could be Pellethane®, which is available in different variants. The second tube member 73 may also comprise polyurethane. At the other end of the second tubular member 73, the second tubular member 73 is joined to a first branch of a preferably T-shaped bifurcated section 75. The bifurcated section has s second branch which provides the entry port to the working channel together with a connector 76 or lead-in mounted on the chassis 12. In the preferred embodiment shown the bifurcated section is 75 T-shaped. That is to say perpendicular that the second branch is perpendicular to the first branch. Evidently the second branch could also be arranged a different angle, so as to provide more of a Y-shape. The connector 76 allows a suction means to be attached for extracting fluid from a body cavity via the working channel. Alternatively a fluid source may be attached to the connector 76, allowing e.g. irrigation or aspiration of the body cavity via the working channel. The third branch of the bifurcated section 75 is preferably aligned with the first branch so as to provide an unobstructed straight passage through the bifurcated section 75 for the first and second motion transfer members 53, 54. To the third branch of the bifurcated section a first end of a third tubular member is attached, which at least in the released position of the operating member 22 is aligned with the first and third branch of the bifurcated section 75 and the second tubular member 73, when the latter is in a relaxed position, i.e. not influenced by external forces from body cavity walls or the like. The second end of the third tubular member 71 forms the proximal end of the working channel, and is terminated in an end sealing means 51. As described above end sealing means, not only seals the proximal end of the working channel, but also serves as part a first kinematic chain by being pivotally connected to the first lever 48. The third tubular member 71 is preferably in the form of a hose of a highly flexible material, as compared to the remainder of the tubular members forming the working channel. The hose could be provided with corrugations or the like to from a bellows. Making the third tubular member of a highly flexible material serves two purposes.

The first purpose is that it allows the length of the working channel to adapt to the movement of the members of the first kinematic chain in particular the first lever 48, the first motion transfer member 53 and the interposed end sealing member 51. The flexible material allows the working channel to deform in order to adapt in length to accommodate the movement of the first motion transfer member. However, by being flexible the material also allows working channel to deform in order to comply with the swinging movement of the end sealing member caused by the first lever 48 moving the end sealing member 51 out of alignment with the first and third branches of the bifurcated member 75 and second tubular member 73. By being able to comply with these movements, the third tubular member 71 allows transfer of movement using parts of the working cannel itself, in turn, allowing transfer of movement from the operating means 22 to the tool 55 without breaching the integrity of working channel wall. Undesired ingress of pollutants is thus avoided.

The second purpose is similar to the first purpose, because by being flexible the material also allows working channel to deform in order to comply with the movement of the members of the second kinematic chain, in particular the movement of the first tubular end member 52 caused by the second lever 49 in conjunction with the arm first 50. As mentioned above this movement is transferred via the working channel wall, because the third tubular member 72 is clamped between the first tubular end member 52 and clamping member 79. By being able to comply with these movements, the third tubular member 71 allows transfer of movement using parts of the working cannel itself, in turn, allowing transfer of movement from the operating means 22 to the tool 55 without breaching the integrity of working channel wall. Undesired ingress of pollutants is thus avoided.

Clamping the third tubular member 72 in this way between the clamping member 79 and first tubular end member 52, provide minor problems which the present invention also overcomes. One problem is to ensure good grip so that the relative position between the clamping member 79 and the first tubular end member 52 does not change due to the forces in the kinematic chain when the tool 55 is operated. The first tubular end member 52 the first tubular end member may comprise concentric ribs 98 or corrugations, or similar means. A second problem is with this configuration of the working channel with a sealed appendix at the proximal end, the output port at the distal end, and entry port located between them, it becomes difficult to sterilize the interior of the appendix, in particular the proximal end thereof between the end sealing means 51 and the first tubular end member 52, because the access of sterilizing fluid, such as Ethylene Oxide, may be blocked by the first tubular end member 52. Sterilisation with Ethylene Oxide (ETO sterilization) is preferred for sterilisation, because the endoscope 1 according to the invention is preferably a disposable endoscope made from low cost materials, which may not necessarily withstand other sterilization processes such as the high temperature and pressure of an autoclave sterilisation.

Accordingly, as can be seen in FIG. 15a an elongate groove along the first tubular end member 52 and across the concentric ribs 98 is provided. In assembly this groove is made to register with gap in the clamping means 79, so as to allow an open fluid passage along the first tubular end member 52. Preferably, the inner diameter of the third tubular member 71 is selected to be larger than the largest outer diameter of the first tubular end member 52 so as to form a pouch in the first tubular member 71 also registering with the groove 99.

A third problem is that using the working channel wall as a part of the kinematic chains, and therefore in the second kinematic chain gripping and the third tubular member 71 somewhere between the sealing end member 51 and the bifurcated section 75, may cause inadvertent overstretching of the flexible material of the third tubular member, leading, in turn, to an undesired rupture of the working channel wall. To overcome this, a strike plate 59 is provided in the chassis 12. When the clamping member 79 is moved under the by depression of the operating member 22 by the operator, the clamping member will strike the underside (as understood with reference to FIG. 1) of the strike plate 59, and will be limited in further motion. Thus even if the operator presses inappropriately hard on the operating member 22, the clamping means will not tear the third tubular member 71 and breach the integrity of the working channel wall. Preferably, the strike plate serves the dual purpose of also accommodating electronics of the endoscope 1 such as a printed circuit board 62.

The present invention thus provides an endoscope with a working channel, used not only for accommodating parts of the control mechanism of a tool but also forming itself a part of the control mechanism. The skilled person will understand that the arrangements described above, and in particular the kinematic chains are only exemplary embodiments, and that the endoscope according to the present invention may be devised in many different variants without departing from the scope of the invention as expressed in the claims.

What is claimed is:

1. An endoscope comprising:
    a handle with a handle housing;
    an insertion tube extending from the handle with a bending section at a distal end of the insertion tube and terminating in a tip part of the bending section, the bending section comprising a distal end segment, an intermediate segment, and a plurality of articulated bending segments, wherein the intermediate segment is connected to and between the distal end segment and the plurality of articulated bending segments, and wherein the intermediate segment is longer than a bending segment from the plurality of articulated bending segments;
    a first operating member at the handle housing for controlling the bending section;
    a working channel extending within the insertion tube and having a distal end and a proximal end;
    a tool operating member at the handle housing;

a retractable tool;
a motion transfer member connected to and between the retractable tool and the tool operating member, the motion transfer member extending within the working channel to operate the retractable tool at an exit port of the distal end of the working channel at the tip part in response to the activation of the tool operating member, wherein a distal end of the motion transfer member comprises a rigid tube section, which is more rigid than the rest of the motion transfer member.

2. The endoscope of claim 1, wherein the distal end segment is longer than the bending segment from the plurality of articulated bending segments.

3. The endoscope of claim 1, wherein the motion transfer member comprises an inner motion transfer member and an outer motion transfer member.

4. The endoscope of claim 3,
wherein the working channel is formed by a tube that comprises at least a first proximal section and a second distal section with a first connecting transition connecting the two sections,
wherein the second section has a higher degree of flexibility than the first section,
wherein the outer motion transfer member comprises at least two sections differing from each other in rigidity and with a second connecting transition connecting the two sections, and
wherein the first connecting transition and the second connecting transition are staggered with respect to each other along the length of the insertion tube.

5. The endoscope of claim 1, wherein movement of the first operating member is limited by the interior of the handle housing.

6. The endoscope of claim 5, wherein the handle housing comprises an interior chassis carrying the first operating member, and wherein the chassis comprises stop members limiting movement of the first operating member.

7. An endoscope comprising:
a handle including a handle housing having an interior, a bending portion operator extending partially through the handle housing, and a tool operator extending partially through the handle housing;
an insertion tube extending from the handle and including a bending section connected to the bending portion operator and terminating in a tip part having an exit port, the insertion tube including a working channel extending within the insertion tube and having a proximal end and a distal end; and
a motion transfer member extending at least partly within the working channel and comprising a rigid tube section and a portion less rigid than the rigid tube section, the motion transfer member and the tool operator configured to connect to a retractable tool positioned at the distal end of the working channel, wherein in a released position the tool operator is configured to at least partially position the retractable tool in the bending section, wherein in an intermediate position the tool operator is configured to position the retractable tool in an extended position wherein the retractable tool extends past the exit port, and wherein in a depressed position the tool operator is configured to position the retractable tool in the extended position and to extend the rigid tube section to at least partially overlap the retractable tool thereby actuating the retractable tool, and wherein the intermediate position is intermediate the extended position and the depressed position.

8. The endoscope of claim 7, wherein the rigid tube section is more rigid than the rest of the motion transfer member.

9. The endoscope of claim 7, wherein the motion transfer member comprises an inner motion transfer member and an outer motion transfer member.

10. The endoscope of claim 7, wherein the interior of the handle housing is configured to limit movement of the bending portion operator.

11. The endoscope of claim 7, wherein the handle housing comprises an interior chassis configured to carry the bending portion operator, and wherein the chassis comprises stop members configured to limit movement of the bending portion operator.

12. An endoscope comprising:
a handle including a handle housing having an interior, a bending portion operator extending partially through the handle housing, and a tool operator extending partially through the handle housing;
an insertion tube extending from the handle and including a bending section connected to the bending portion operator and terminating in a tip part having an exit port, the insertion tube including a working channel extending within the insertion tube and having a proximal end and a distal end;
a motion transfer member extending at least partly within the working channel and comprising a rigid tube section and a portion less rigid than the rigid tube section; and
a retractable tool positioned at the distal end of the working channel and connected by the motion transfer member to the tool operator,
wherein, in a released position of the tool operator, the retractable tool is at least partially positioned in the bending section, in an intermediate position of the tool operator, the retractable tool extends past the exit port to an extended position, and in a depressed position of the tool operator, the retractable tool is in the extended position and the rigid tube section is extended and at least partially overlaps the retractable tool thereby actuating the retractable tool,
wherein the intermediate position is intermediate the extended position and the depressed position.

13. The endoscope of claim 12, wherein the rigid tube section is more rigid than the rest of the motion transfer member.

14. The endoscope of claim 12, wherein the motion transfer member comprises an inner motion transfer member and an outer motion transfer member.

15. The endoscope of claim 12, wherein the interior of the handle housing is configured to limit movement of the bending portion operator.

16. The endoscope of claim 12, wherein the handle housing comprises an interior chassis configured to carry the bending portion operator, and wherein the chassis comprises stop members configured to limit movement of the bending portion operator.

17. An endoscope comprising:
a handle with a handle housing;
an insertion tube extending from the handle with a bending section at a distal end of the insertion tube and terminating in a tip part of the bending section, the bending section comprising a distal end segment, an intermediate segment, and a plurality of articulated bending segments, wherein the intermediate segment is connected to and between the distal end segment and the plurality of articulated bending segments, and wherein the intermediate segment is longer than a bending segment from the plurality of articulated bending segments;
a first operating member at the handle housing for controlling the bending section;
a working channel extending within the insertion tube and having a distal end and a proximal end;
a tool operating member at the handle housing;
a retractable tool;
a motion transfer member connected to and between the retractable tool and the tool operating member, the motion transfer member extending within the working channel to operate the retractable tool at an exit port of the distal end of the working channel at the tip part in response to the activation of the tool operating member,
wherein the motion transfer member comprises an inner motion transfer member and an outer motion transfer member, wherein the working channel is formed by a tube that comprises at least a first proximal section and a second distal section with a first connecting transition connecting the two sections, wherein the second section has a higher degree of flexibility than the first section, wherein the outer motion transfer member comprises at least two sections differing from each other in rigidity and with a second connecting transition connecting the two sections, and wherein the first connecting transition and the second connecting transition are staggered with respect to each other along the length of the insertion tube.

* * * * *